(12) United States Patent
Nagasu et al.

(10) Patent No.: US 6,986,990 B1
(45) Date of Patent: Jan. 17, 2006

(54) POLLEN ALLERGY-RELATED GENE 513

(75) Inventors: Takeshi Nagasu, Ibaraki (JP); Yuji Sugita, Kanagawa (JP); Tomoko Fujishima, Tokyo (JP); Tadahiro Oshida, Kanagawa (JP); Masaya Obayashi, Tokyo (JP); Shigemichi Gunji, Tokyo (JP); Izumi Obayashi, Kanagawa (JP); Yukiho Imai, Kanagawa (JP); Nei Yoshida, Kanagawa (JP); Kaoru Ogawa, Kanagawa (JP); Keiko Matsui, Kanagawa (JP)

(73) Assignee: Genox Research, Inc., (JP)

( * ) Notice: Subject to any disclaimer, the term of this patent is extended or adjusted under 35 U.S.C. 154(b) by 0 days.

(21) Appl. No.: 10/019,832

(22) PCT Filed: Apr. 26, 2000

(86) PCT No.: PCT/JP00/02733

§ 371 (c)(1),
(2), (4) Date: Mar. 28, 2002

(87) PCT Pub. No.: WO00/65049

PCT Pub. Date: Nov. 2, 2000

(30) Foreign Application Priority Data

Apr. 27, 1999 (JP) ................................ 11/120491

(51) Int. Cl.
*C12Q 1/66* (2006.01)
(52) U.S. Cl. .......................................... 435/6; 435/91.2
(58) Field of Classification Search .................... 435/6, 435/91.2; 536/23.1, 24.31
See application file for complete search history.

(56) References Cited

U.S. PATENT DOCUMENTS 5,792,850 A * 8/1998 Baumgartner et al. ..... 536/23.5
6,610,481 B2 * 8/2003 Koch ............................ 435/6

FOREIGN PATENT DOCUMENTS

JP         11-332567 A      12/1999

OTHER PUBLICATIONS

Leung, D.Y.M. "Molecular Basis of Allergic Diseases," *Molecular Genetics and Metabolism*, 63:157-167 (1998).
Yanagihara et al., "Allergen-Specific Human IgE Helper T Cell Lines Derived from Patients Allergic to Japanese Cedar Pollen," *Int. Arch. Allergy Immunol.*, 105:162-170 (1994).
Database EMBL "Online", EBI Oct. 16, 1997, Database accession No. AA623116, XP-002238625.
Database EMBL "Online", EBI Aug. 25, 1995, Database accession No. HS111C05B, XP-02238715.
Database EMBL "Online", EBI Aug. 20, 1996, Database accession No. HSA28892, XP-002238716.
Holroyd et al., "asthma and Bronchial Hyperresponsiveness Linked to the XY Long Arm Pseudoautosomal Region," *Genomics*, 52:233-235 (1998).
Honda, K., "Immunogenetic analysis of Cryptomeria Pollinosis Evidence for the HLA-Linked Immune Suppression Gene to Cryptomeria Japoniea Pollen Antigen,"*Fukuoka Acta Med.* 80(1):28-37 (1989). Abstract Only in English.
Munakata, M., "Beta-Adrenergic Receptor Gene," *Gendai Iryo*, 30(3):863-867 (1998).
Takabayashi et al., "Novel polymorphism in the 5'-untranslated region of the interleukin-4 gene," *J. Hum Genet.*, 44(5):352-353 (1999).

* cited by examiner

*Primary Examiner*—Jullet C. Switzer
(74) *Attorney, Agent, or Firm*—Townsend and Townsend and Crew LLP (57) ABSTRACT

T cells from multiple subjects who showed different cedar pollen specific IgE titers were prepared before and after cedar pollen dispersal, and differential display analysis was performed to screen for pollen antigen responsive genes. As a result, a novel gene was successfully isolated whose expression is significantly higher in subjects with high cedar pollen specific IgE titer. The inventors have found that it is possible to use this gene to test for an allergic disease and to screen for candidate compounds for therapeutic drugs for an allergic disease.

6 Claims, 2 Drawing Sheets

SEQUENCE LISTING

<160> NUMBER OF SEQ ID NOS: 9

<210> SEQ ID NO 1
<211> LENGTH: 1171
<212> TYPE: DNA
<213> ORGANISM: Homo sapiens

<400> SEQUENCE: 1

```
actcactata gggctcgagc ggcgcccggg caggtatacc ttcggtgttt ttgagaatct      60
gagaatgatg gaggagaaat ggaaagatag gaatagaaag agattacatt aggaattaaa     120
tttcttgttc ctcttttct gatatgaaac caaattggag gttagatcat ccagaaagag     180
aattcagtgt tttccagttt tccaacctgc ttgctcataa gaatgacttg gagtggtaga     240
```

-continued

```
tcttgattca gtcgttctga ggatagcaca aagaatttgt attttttagca aacactctcc      300 atgattatag tattatatgg gaattaaact taaaccttct ttaaataaag ccccccaagtt      360 tgacccatta gctcagctat agaattactg aatatttta gtatggcaat actgtcaaga       420
aaaagcactt tataatgtgc ttaaatttct ttcttccctt tcctttcttt ctttctttct      480
ttctttcttt ctttctttct ttcttttgg aaaagtttaa ggctatataa aaaatagaga      540
gaatggggct tctcgctatg ctcagcctgt gtgtcatcat tactgtcatg ctggccattg      600
ttctctgctg ctgtgcccgg gccctgaggc ctccttcacc tctatcccca ccaccactat      660
ccagtcagtt tgctgctgct tccgtggttc acatgaggca gatgaggagt ttgatgcatg      720
ctgggtgaca tgcttcaaca agccagagat agatgcctgg gaattgcata agaattgaa       780 cacacttgct ggctatgacc tggttccaga accccaaatc attgatgttg cttcgcaggc      840
atgcagacag ttcgatgctt ttcctagggc agtttgcatc ctagaggttg ttaaggacaa      900
ggcaggacct cataagaaaa tgtcatccaa gaactcagac caactttaaa tgaattggga      960
atccccactc cagaggacct aggcttagac aaagtgtgaa ccccagggac aagcgttcca     1020 gggattatt ggtattgcta cttgattgta aacactcccc tggaaatgct gatgataaca     1080 tgttaccta tttgaacacc tttttctta ttgaataccw aaccatgtta tggtaacttg      1140
gactttaata aagggaaat gagtttgaac t                                    1171

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 2 gtttttttt tttttta                                                      17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 3 gtttttttt tttttc                                                       17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4 gtttttttt tttttg                                                       17

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence:Artificially
```

```
-continued
        Synthesized Primer Sequence

<400> SEQUENCE: 5
tcatgcagac                                                              10

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:Artificially
        Synthesized Primer Sequence

<400> SEQUENCE: 6
gcagacagtt cgatgctttt cc                                                22

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:Artificially
        Synthesized Primer Sequence

<400> SEQUENCE: 7
ttttcttatg aggtcctgcc ttg                                               23

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:Artificially
        Synthesized Probe Sequence

<400> SEQUENCE: 8
agggcagttt gcatcctaaa ggttgttaag g                                      31

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:Artificially
        Synthesized Primer Sequence

<400> SEQUENCE: 9
gcttgtccct ggggttcaca ctt                                               23
```

POLLEN ALLERGY-RELATED GENE 513

TECHNICAL FIELD

The present invention relates to a gene involved in allergic disease, in particular, pollen allergy, and a method for testing for an allergic disease and a method for screening for a candidate compound for a therapeutic drug for an allergy using the expression of the gene as an index.

BACKGROUND ART

Allergic diseases including pollen allergy are considered to be multifactorial diseases. These diseases involve the expression of many different genes each of which is influenced by various environmental factors. Thus, it is very difficult to identify a specific gene which causes a specific disease.

Additionally, allergic diseases are thought to involve the expression of mutated or defective genes, or overexpression or reduction of the specific gene expression. To elucidate the role of gene expression in diseases, it is necessary to understand how a gene is involved in triggering disease onset and how expression of the gene is altered by external stimulants such as drugs.

Recent developments in gene expression analysis techniques have made it possible to analyze and compare the gene expression of many clinical samples. Among these methods, the differential display (DD) method is significantly useful. The differential display method was originally developed by Liang and Pardee in 1992 (Science, 1992, 257:967–971). By using this method, one can screen several tens or more different samples at one time and it is possible to detect altered gene expression among the samples. By revealing alterations in gene expression due to mutation as well as time- and environment-dependent gene expression, it is expected to provide important information about disease-related genes. Such genes include those of which expression is influenced by environmental factors.

Among allergic diseases, pollen allergy has recently become more common. It is considered that some genes whose expression is affected by pollen, one of the environmental factors, are involved in cause of pollen allergy. Based on this situation, it was hoped that genes involved in pollen allergy could be isolated.

DISCLOSURE OF THE INVENTION

An objective of the present invention is to provide a gene involved in allergic disease, in particular, pollen allergy. Another objective of the invention is to provide a method for testing for an allergic disease and a method for screening for a candidate compound for a therapeutic drug for an allergy using the expression of the gene as an index.

According to the previously established techniques of the "Fluorescent DD method" (T. Ito et al. FEBS Letter 351: 231–236, 1994), the inventors developed a new DD system that can analyze T-cell RNA samples prepared from multiple human blood samples. The inventors isolated T cells from blood samples of multiple subjects including pollen allergy patients before and after exposure to pollen dispersal and conducted screening for a gene showing differential expression between subjects showing different cedar pollen-specific IgE titers, or before and after pollen dispersal. The inventors thus isolated a novel gene (gene 513).

The inventors divided the subjects into those with a high IgE titer against cedar pollen (cedar pollen allergy diathesis group) and others (normal group) and measured the expression level of the isolated gene 513 between the two groups. The results showed that the gene expression level was significantly higher in the cedar pollen allergy diathesis group compared to the normal group. Based on these observations, the inventors found that the gene expression level can be used as an index to test for an allergic disease and to screen for candidate compounds for a therapeutic drug for allergic diseases.

Therefore, the present invention relates to a gene showing high expression in individuals having the allergy diathesis and a method for testing for an allergic disease and a method for screening for a candidate compound for a therapeutic drug for allergic diseases using the gene expression as an index. More specifically, the present invention relates to:

(1) a nucleic acid molecule comprising the nucleotide sequence of SEQ ID NO: 1;

(2) a nucleic acid molecule comprising the coding region of the nucleotide sequence of SEQ ID NO: 1;

(3) a DNA that specifically hybridizes to the nucleic acid molecule of (1) or (2) and that is at least 15 nucleotides long;

(4) a method for detecting the nucleic acid molecule of (1) wherein said method uses the DNA of (3);

(5) a method for testing for an allergic disease, said method comprising the steps of:
   (a) preparing T cells from a subject,
   (b) preparing an RNA sample from said T cells,
   (c) conducting hybridization with said RNA sample using the DNA of (3) as probe, wherein said DNA is labeled, and
   (d) measuring the amount of RNA that is derived from said subject and that hybridizes with said DNA and comparing said amount with a control (normal group);

(6) a method for testing for an allergic disease, said method comprising the steps of:
   (a) preparing T cells from a subject,
   (b) preparing an RNA sample from said T cells,
   (c) synthesizing cDNA by conducting reverse transcription reaction with said RNA sample,
   (d) conducting polymerase chain reaction (PCR) using said cDNA as template and the DNA of (3) as primer, and
   (e) comparing the amount of a DNA amplified by said PCR with a control (normal group);

(7) the method of (6), wherein said PCR is carried out by a PCR amplification monitoring method;

(8) the method of any one of (5) to (7), wherein said T cells are prepared from peripheral blood of said subject;

(9) the method of any one of (5) to (8), wherein said allergic disease is a cedar pollen allergy;

(10) a method for screening for a candidate compound for a therapeutic drug for an allergic disease, said method comprising the steps of:
   (a) administering a test compound to a pollen allergy model animal and stimulating with pollen antigen,
   (b) preparing T cells from said model animal,
   (c) preparing an RNA sample from said T cells,
   (d) conducting hybridization with said RNA sample using the DNA of (3) as probe, wherein said DNA is labeled,
   (e) measuring the amount of RNA that is derived from said T cells and that hybridizes with said DNA, and
   (f) selecting a compound that reduces the amount of said RNA measured in (e), compared to a control (a case where said test compound is not administered);

(11) a method for screening for a candidate compound for a therapeutic drug for an allergic disease, said method comprising the steps of:
  (a) administering a test compound to a pollen allergy model animal and stimulating with pollen antigen,
  (b) preparing T cells from said model animal,
  (c) preparing an RNA sample from said T cells,
  (d) synthesizing cDNA by conducting reverse transcription reaction with said RNA sample,
  (e) conducting polymerase chain reaction (PCR) using said cDNA as template and the DNA of (3) as primer, and
  (f) selecting a compound that reduces the amount of said DNA amplified in (e), compared to a control (a case where said test compound is not administered);

(12) a method for screening for a candidate compound for a therapeutic drug for an allergic disease, said method comprising the steps of:
  (a) administering a test compound to a pollen allergy model animal,
  (b) preparing lymphocytes from said model animal,
  (c) stimulating said lymphocytes with pollen antigen,
  (d) separating T cells from said lymphocytes stimulated with said antigen,
  (e) preparing an RNA sample from said T cells,
  (f) conducting hybridization with said RNA sample using the DNA of (3) as probe, wherein said DNA is labeled,
  (g) measuring the amount of RNA that is derived from said T cells and that hybridizes with said DNA, and
  (h) selecting a compound that reduces the amount of said RNA measured in (g), compared to a control (a case where said test compound is not administered);

(13) a method for screening for a candidate compound for a therapeutic drug for an allergic disease, said method comprising the steps of:
  (a) administering a test compound to a pollen allergy model animal,
  (b) preparing lymphocytes from said model animal,
  (c) stimulating said lymphocytes with pollen antigen;
  (d) separating T cells from said lymphocytes stimulated with said antigen,
  (e) preparing an RNA sample from said T cells,
  (f) synthesizing cDNA by conducting reverse transcription reaction with said RNA sample,
  (g) conducting polymerase chain reaction (PCR) using said cDNA as template and the DNA of (3) as primer, and
  (h) selecting a compound that reduces the amount of said DNA amplified in (g), compared to a control (a case where said test compound is not administered);

(14) a method for screening for a candidate compound for a therapeutic drug for an allergic disease, said method comprising the steps of:
  (a) preparing lymphocytes from a pollen allergy model animal or from a human having a pollen allergy,
  (b) stimulating said lymphocytes with pollen antigen in the presence of a test compound,
  (c) separating T cells from said lymphocytes stimulated with said antigen,
  (d) preparing an RNA sample from said T cells,
  (e) conducting hybridization with said RNA sample using the DNA of (3) as probe, wherein said DNA is labeled,
  (f) measuring the amount of RNA that is derived from said T cells and that hybridizes with said DNA, and
  (g) selecting a compound that reduces the amount of said RNA measured in (f), compared to a control (a case where said test compound is not administered);

(15) a method for screening for a candidate compound for a therapeutic drug for an allergic disease, said method comprising the steps of:
  (a) preparing lymphocytes from a pollen allergy model animal or from a human having a pollen allergy,
  (b) stimulating said lymphocytes with pollen antigen in the presence of a test compound,
  (c) separating T cells from said lymphocytes stimulated with said antigen,
  (d) preparing an RNA sample from said T cells,
  (e) synthesizing cDNA by conducting reverse transcription reaction with said RNA sample,
  (f) conducting polymerase chain reaction (PCR) using said cDNA as template and the DNA of (3) as primer, and
  (g) selecting a compound that reduces the amount of said DNA amplified in (f) compared to a control (a case where said test compound is not administered);

(16) a method for screening for a candidate compound for a therapeutic drug for an allergic disease, said method comprising the steps of:
  (a) stimulating a T-cell line with a lymphocyte-stimulating substance in the presence of a test compound,
  (b) preparing an RNA sample from said stimulated T-cell line,
  (c) conducting hybridization with said RNA sample using the DNA of (3) as probe, wherein said DNA is labeled,
  (d) measuring the amount of RNA that is derived from said T-cell line and that hybridizes with said DNA, and
  (e) selecting a compound that reduces the amount of said RNA measured in (d), compared to a control (a case where said test compound is not administered);

(17) a method for screening for a candidate compound for a therapeutic drug for an allergic disease, said method comprising the steps of:
  (a) stimulating a T-cell line with a lymphocyte-stimulating substance in the presence of a test compound,
  (b) preparing an RNA sample from said stimulated T-cell line,
  (c) synthesizing cDNA by conducting reverse transcription reaction with said RNA sample,
  (d) conducting polymerase chain reaction (PCR) using said cDNA as template and the DNA of (3) as primer, and
  (e) selecting a compound that reduces the amount of said DNA amplified in (d), compared to a control (a case where said test compound is not administered);

(18) the method of (10) or (11), wherein said T cells are prepared from peripheral blood of said pollen allergy model animal;

(19) the method of any one of (12) to (15), wherein said lymphocytes are prepared from peripheral blood; and (20) the method of any one of (10) to (19), wherein said allergic disease is a cedar pollen allergy.

In the present invention allergic disease is a general term for diseases that involve allergic reactions. More specifically, for a disease to be considered allergic, the allergen there must be identified, there exists a strong correlation between exposure to the allergen and the onset of the pathological change, and the pathological change has been proven to have an immunological mechanism. An immunological mechanism means that the T cells show an immune response to allergen stimulation. Representative allergic diseases are bronchial asthma, allergic rhinitis, atopic dermatitis, pollen allergy, insect allergy, etc. Allergic diathesis is a genetic factor which is inherited from allergic parents to children. Familial allergic diseases are also called atopic diseases, and their causative factor which can be inherited is atopic diathesis.

In the present invention, "nucleic acid molecule" includes DNA and RNA. Also in the present invention, "testing for an allergic disease" includes not only testing a patient who has been affected with the disease but also testing a subject who has not affected with the disease for whether the subject has an allergic diathesis or not.

The present invention relates to a novel gene 513 that correlates with IgE production response against cedar pollen in individuals. The nucleotide sequence of gene 513 cDNA which was found by the inventors is shown in SEQ ID NO: 1.

The nucleotide sequence of gene 513 cDNA which was isolated by the inventors is a partial sequence of 513 cDNA, but one skilled in the art can usually isolate the full length cDNA of gene 513, based on the sequence information of 513 cDNA described in SEQ ID NO: 1. Examples of methods for isolating the full length cDNA include a method for screening a T-cell cDNA library and such by hybridization using a gene 513-derived sequence as a probe and a method for obtaining the full length of the cDNA by screening libraries with an amplification product to be obtained having a primer-specific size as an index using gene 513-derived sequences as primers and using the T-cell cDNA library and such as a template. The examples further include a method for extending the sequence of gene 513 by the RACE method (Frohman, M. A. et al.: Proc. Natl. Acad. Sci. USA, 85: 8992, 1988), in which mRNAs of T cells and such are converted into single stranded cDNAs by using a gene 513-derived sequence as a primer, an oligomer is attached to the end of the cDNA thus obtained, and then PCR is carried out.

Herein, "nucleic acid molecule comprising the nucleotide sequence of SEQ ID NO: 1" includes the full length gene 513 cDNA which can be isolated from information of the 513 cDNA nucleotide sequence according to SEQ ID NO: 1.

Gene 513 expression was significantly higher in the atopic diathesis group (IgE titer against cedar pollen is 3.5 AU/ml or more) than in the non-atopic diathesis group. Therefore, using gene 513 expression (including transcription to mRNA and translation to protein) as an index, it may be possible to test for an allergic disease and to screen for a candidate compound for a therapeutic drug for allergic diseases.

As a disease that can be a target for the testing and treatment in the present invention, cedar pollen allergy is particularly preferable.

Expression of gene 513 can be detected in testing for an allergic disease in the present invention by using a hybridization technique with nucleic acids which can hybridize with gene 513 as probes or by using a gene amplification technique with DNAs which can hybridize with the gene of the present invention as primers.

The probe or primer used for testing for a disease in the present invention means nucleic acid molecules which specifically hybridize to gene 513 and are at least 15 nucleotide long. Herein "specifically hybridize" means that under normal hybridization conditions, preferably stringent conditions, there is no significant cross hybridization with DNA and/or RNA encoding other genes. Stringent condition means, for example, carrying out hybridization using a probe and transfer membrane at 68° C. in Express Hybridization Solution (CLONTECH) and a final wash of 0.1×SSC, 0.05% SDS at 50° C.

These nucleic acid molecules could be either synthetic or natural ones. Also, labeled DNA is usually used as the probe for hybridization. The labeling methods may be nick translation using DNA polymerase I, end labeling using polynucleotide kinase, fill-in end labeling using Klenow fragment (Berger S L, Kimmel A R. (1987) Guide to Molecular Cloning Techniques, Method in Enzymology, Academic Press; Hames B D, Higgins S J (1985) Genes Probes: A Practical Approach. IRL Press; Sambrook J, Fritsch E F, Maniatis T. (1989) Molecular Cloning: a Laboratory Manual, 2nd Edn. Cold Spring Harbor Laboratory Press), transcription labeling using RNA polymerase (Melton D A, Krieg, P A, Rebagkiati M R, Maniatis T, Zinn K, Green M R. (1984) Nucleic Acid Res., 12, 7035–7056), non-isotopic DNA labeling techniques by incorporating modified nucleotides (Kricka L J. (1992) Nonisotopic DNA Probing Techniques. Academic Press), etc.

For testing for an allergic disease using hybridization techniques, for example, Northern hybridization, dot blot hybridization, or DNA micro array technique may be used.

As for gene amplification techniques, for example, RT-PCR may be used. Using the PCR amplification monitoring method during the gene amplification step in RT-PCR as described in Example 8, one can obtain a more accurate quantification of gene 513 expression.

In the PCR amplification monitoring method, the target (DNA or reverse transcribed product of RNA) is hybridized to probes that are dual-labeled at both ends with different fluorescent dyes which, in combination, cancel out their fluorescence each other. When the PCR proceeds and the 5'-3' exonuclease activity of Taq polymerase degrades the probe, the two fluorescent dyes become distant from each other and the fluorescence comes to be detected. The fluorescence is detected in real time. By simultaneously measuring for a standard sample in which the copy number of the target is known, it is possible to determine the copy number of the target in the subject sample with the cycle number where PCR amplification is linear (Holland, P. M. et al., 1991, Proc. Natl. Acad. Sci. USA 88:7276–7280; Livak, K. J. et al., 1995, PCR Methods and Applications 4 (6): 357–362; Heid, C. A. et al., Genome Research 6:986–994; Gibson, E. M. U. et al., 1996, Genome Research 6:995–1001). For the PCR amplification monitoring method, for example, ABI PRISM7700 (Perkin Elmer) may be used.

Testing for an allergic disease in the present invention can be also carried out by detecting a protein encoded by gene 513. For such testing methods, for, example, Western blotting analysis, immunoprecipitation, or ELISA using antibody against the protein encoded by gene 513 may be used.

Antibodies against the protein encoded by the gene 513 of the present invention, may be produced as polyclonal or monoclonal antibody by techniques known to one skilled in the art (Milstein C, et al., 1983, Nature 305 (5934): 537–40). Protein or its partial peptide used as an antigen may be obtained, for example, by inserting gene 513 or its partial sequence into an expression vector, by introducing it into an appropriate host cell to prepare a transformant, by culturing the transformant to express the recombinant protein, and by purifying the expressed recombinant protein from the cultured transformant or the culture supernatant.

In testing for an allergic disease in the present invention, if expression of the gene of the invention is significantly higher in a subject, the subject may be determined to have allergic diathesis with high IgE titer against an allergen such as cedar pollen antigen. It is possible to use the expression level of the gene of the invention together with allergen specific antibody titer, symptoms, and such for testing for an allergic disease.

Expression of gene 513 in T cells is increased in the pollen allergy patient group, which shows high levels of pollen antigen specific IgE. Allergic patients who show response toward antigens except cedar pollen may also give high expression of gene 513 when the T-cell response is accelerated by the antigens. In such a case, increased expression of gene 513 corresponds to an acceleration of the T-cell response, and thus by monitoring the expression level of gene 513, it is possible to screen for therapeutic drugs for an allergic disease.

Methods for screening for a candidate compound for the treatment of allergic disease in this invention can be carried out in vivo or in vitro. In the in vivo screening, for example, model animals such as mice may be administered with a candidate agent and stimulated with pollen antigen. Then T cells are prepared from peripheral blood to measure the transcript product level of gene 513. Alternatively, after administrating a candidate agent to model animals such as mice, lymphocytes are separated from peripheral blood and stimulated by cedar pollen antigen and such in vitro. After the stimulation, T cells are prepared from the lymphocytes, and the transcript product level of gene 513 is measured. As a result of this measurement, a compound which can reduce transcription level of gene 513 may be selected. Here, the stimulation by pollen antigen is carried out to trigger an antigen-specific allergic response in T cells and to judge the treatment effect of the candidate compound on the response.

In an in vitro screening, for example, peripheral blood lymphocytes from a pollen-allergic person, mouse, and such are collected and stimulated by cedar pollen antigen in vitro. At the time of in vitro stimulation, a candidate compound is added. Then T cells are prepared from the stimulated peripheral blood lymphocytes, and the transcript product levels of gene 513 are measured. As a result of this measurement, a compound which can reduce transcription level of gene 513 may be selected.

For screening for a candidate compound for a therapeutic drug for an allergic disease in this invention, a T-cell line may be used. For example, a T-cell line such as the Molt4 or Jurkat T-cell line may be stimulated by a lymphocyte stimulating substance in vitro. As for the lymphocyte stimulating substance, for example, calcium ionophore (A23187), PMA, or phytohemagglutinin (PHA) may be used. At the time of in vitro stimulation, the candidate agent is added. Then the transcript product level of gene 513 is measured in the T-cell line. As a result of this measurement, a compound which can reduce transcription level of gene 513 may be selected.

Like testing for an allergic disease in the invention, expression of gene 513 can be detected in screening for a candidate compound for a therapeutic drug for an allergic disease by using a hybridization technique with nucleic acids which can hybridize with gene 513 as probes or by using a gene amplification technique with DNAs which can hybridize with the gene of the present invention as primers.

As for hybridization techniques, for example, Northern hybridization, dot blot hybridization, or DNA micro array technique may be used. As for gene amplification techniques, for example, RT-PCR may be used. Using the PCR amplification monitoring method as described in Example 8 during the gene amplification step in RT-PCR, one can more accurately quantify the gene 513 expression.

Test compounds used in such screening include compound preparations synthesized by existing chemical methods such as steroid derivatives, compound preparations synthesized by combinatorial chemistry, extracts from animal or plant tissues, mixtures of multiple compounds such as microbial cultures and their purified preparations.

The compound isolated by the method for screening for a candidate compound for a therapeutic drug for an allergic disease in this invention can be a candidate agent for improving the condition of individuals having allergic diathesis against allergens such as pollen antigen.

When a compound isolated by the screening method of the present invention is used as a drug, it can be formulated by any known pharmaceutical manufacturing methods. For example, the compound is administered to patients with a pharmaceutically acceptable carrier or medium (e.g. physiological saline, vegetable oil, suspending agent, surfactant, stabilizer, etc.) The drug can be administered via various routes, for example, percutaneously, intranasally, transbronchially, intramuscularly, intravenously, or orally, depending on the properties of the compound. Dosage may vary depending on some factors, such as age, weight, condition of the patient and the administration method, but those skilled in the art can properly determine the suitable dosage.

BEST MODE FOR CARRYING OUT THE INVENTION

The present invention will be explained in detail below with reference to examples, but is not to be construed as being limited thereto.

EXAMPLE 1

Blood Sample Collection from 10 Adult Volunteers

To collect T cells before and after cedar pollen dispersal, 10 ml blood samples were collected from 10 adult volunteers (A to J) before and after exposure to cedar pollen dispersal. The first blood sample was obtained before the Japanese cedar pollen dispersal season (January and February, 1997), and the second sampling time was after the Japanese cedar pollen dispersal season (March, April, and May, 1997). From eight people among the volunteers, blood samples were obtained at both periods. From two other people, samples could be obtained only after pollen dispersal season. Parts of the blood samples were used for measuring cedar pollen specific IgE amounts. For the specific IgE measurement, the CAP RAST method (Pharmacia) was employed, which is a modified RAST (radio allergo sorbent test, Wide, L. et, al.: Lancet 2: 1105–1107, 1967) method that uses a paper disk as a solid phase. Serum from Pharmacia which has standard antibody titer was used as the standard to determine the IgE antibody titer in the samples [unit was shown in either Pharmacia RAST Unit, PRU or AU (arbitrary unit)].

Figure 1:
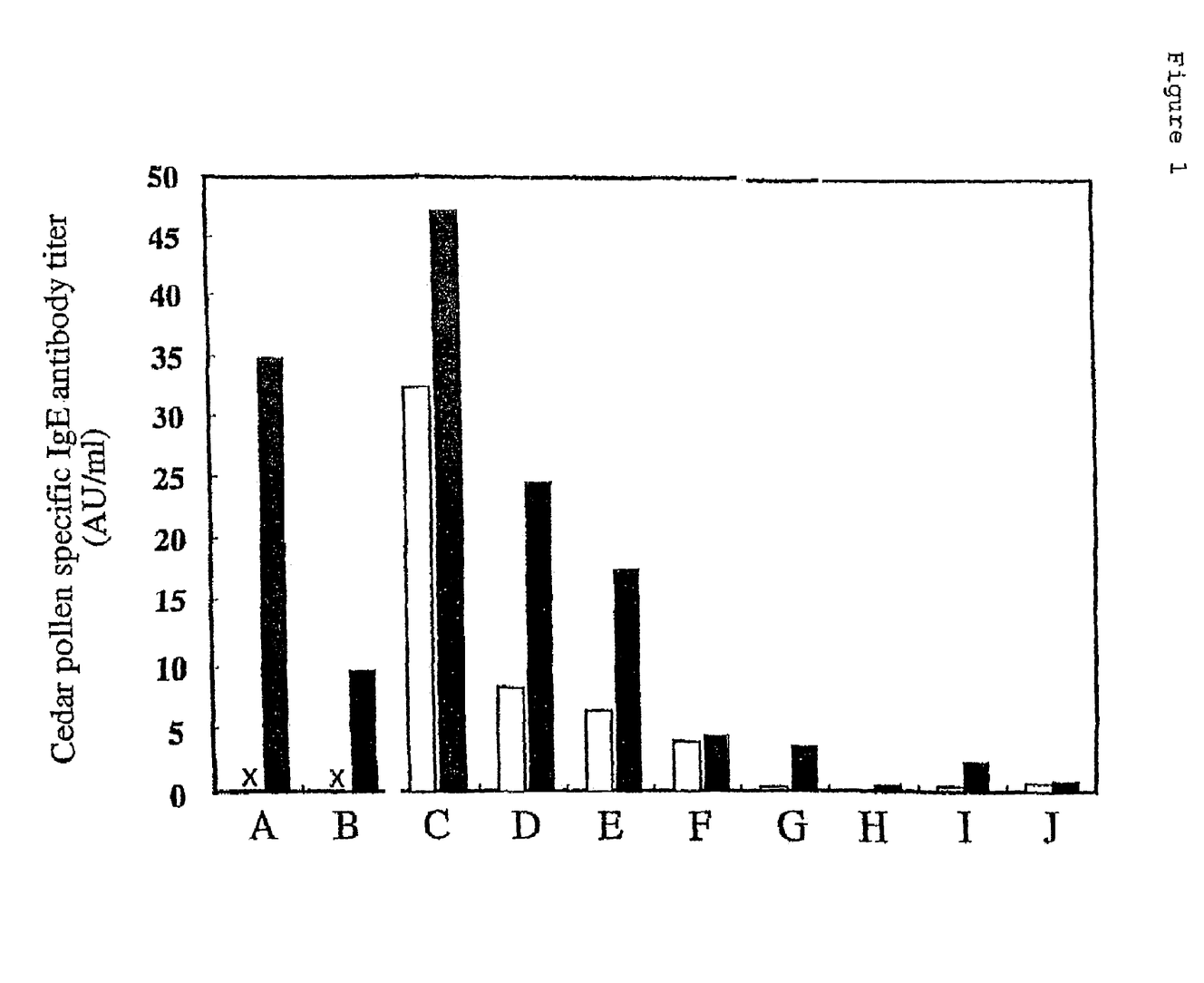
FIG. 1 shows cedar pollen specific IgE antibody titer from a total of 18 blood samples obtained from 10 subjects. The cedar pollen specific IgE antibody titer of each blood sample from subjects A to J (sample number 1 to 18) is indicated in AU/ml. The specific IgE antibody titers in blood samples prepared before (white column, left) and after (black column, right) the dispersal of pollen are depicted in paired columns. Blood samples of subjects A and B were collected only after pollen dispersal.

The cedar pollen specific IgE titers from each subject before and after pollen dispersal are shown in FIG. 1. As the figure indicates, the majority of the 10 subjects showed increases in the concentration of cedar pollen specific IgE in sera after pollen exposure. A CAP RAST test value of cedar pollen specific IgE larger than 2 was used in judging whether a subject had or did not have atopic diathesis. Eight subjects, A to G and I, fell into the atopic diathesis group (will also be called "patient"), and subjects H and J were grouped as healthy (will also be called "normal"). Among the eight in the atopic diathesis group, seven showed allergic rhinitis after pollen dispersal.

EXAMPLE 2

Preparation of Lymphocyte Fractions from Blood Samples

T cells were prepared from 10 ml of blood sample as follows. First, 1 ml of heparin (purchased from Novo or other company) was spread over the syringe wall surface, and then 10 ml of blood sample including a final concentration of 50 units/ml heparin was taken. For blood collection, two 22G needles for each person were prepared. After removing the needle from the syringe, the blood sample was transferred to a 50-ml centrifuge tube (polypropylene). The tube was centrifuged at 1500 rpm for 5 min at room temperature and then 1.1 ml was taken from as close to the surface as possible. After further 15000 rpm centrifugation for 5 min at 4° C., 1 ml of the supernatant was collected as plasma. An equal amount (9 ml) of 0.9% NaCl containing 3% dextran (Nacalai) was added to the remaining sample. This mixture was inverted gently several times, and then let stand for 30 min at room temperature. PRP (platelet rich plasma) was transferred to a new 15 ml centrifuge tube and centrifuged at 1200 rpm (equivalent to 150×g for the Tomy centrifuge) for 5 min at room temperature. After the centrifugation, platelets were present in the supernatant. Precipitated cells were resuspended in 5 ml of Ca, Mg free HBSS (GIBCO, etc.). The cell suspension was layered on the top of a 5 ml Ficoll Paque (Pharmacia)-containing Falcon tube (2006 or 2059, polypropylene) by use of a capillary pipette. After centrifuging the tube at 1200 rpm for 5 min, it was further centrifuged at 1500 rpm. (equivalent to 400×g for the Tomy centrifuge) for 30 min at room temperature. As a result, granulocytes and erythrocytes were precipitated, and lymphocytes, monocytes, and platelets were included in the middle layer, with the Ficoll layer between the precipitate and the middle layer.

The middle layer was collected by a capillary pipette. Two to three volumes of BSA/PBS (0.5% BSA, 2 mM EDTA in PBS, pH 7.2, degassed just before use) were added thereto, and the mixture was centrifuged at 1200 rpm for 5 min at 4° C. The precipitate was collected and washed twice with a BSA/PBS solution. After the second wash, cells were resuspended in 5 ml BSA/PBS, and a portion of the suspension was diluted two-fold with trypan blue to count the cell number. Total cell numbers were about $1\times10^7$, and the suspension was used as lymphocyte fraction.

EXAMPLE 3

T Cell Preparation from the Lymphocyte Fraction

The lymphocyte fraction obtained in Example 2 was centrifuged at 1200 rpm for 5 min at 4° C., and the precipitate was resuspended to $10^8$ cells/100 µl with BSA/PBS. The volume was approximately 20 µl. The cell suspension was transferred to an Eppendorf tube (1.5 ml), and then a CD3 microbead solution was added thereto. This sample was allowed to stand at 4 to 10° C. for 30 min (not on ice) and further treated using magnetic cell sorter (MACS, Miltenyi Biotech Inc.) by the following procedure.

An $MS^+/RS^+$ column was set to Mini MACS or Vario MACS separation unit (without needle). Five hundred µl of BSA/PBS was gently applied onto the column, and the buffer was run off. Then CD3 microbead-labeled cells were applied onto the column. The column was washed three times using 500 µl of BSA/PBS (B-cell fraction). The column was removed from the separation unit and set onto a tube to collect the eluate. One ml of BSA/PBS was applied onto the column, and CD3-positive cells were eluted rapidly using plunger attached with the column. This was used as T-cell fraction.

The obtained T-cell fraction was centrifuged at 1200 rpm at 4° C. for 5 min. The precipitate was washed twice with BSA/PBS. After the second wash, the cells were resuspended in 1 ml of BSA/PBS, and a portion of the suspension was diluted two-fold by trypan blue to count the cell number. Total cell numbers were approximately $4\times10^6$.

EXAMPLE 4

Total RNA Preparation from the T Cells

Total RNA was prepared from T cells using RNeasy Mini (Qiagen) basically following the manufactures' procedures. All the procedures were carried out at room temperature, wearing gloves. Four-fold volume of ethanol was added to wash buffer RPE. To the lysis buffer RLT, 10 µl/ml of 2-mercaptoethanol was added. The cell suspension was centrifuged at 1000 to 1200 rpm for 5 min, and the supernatant was removed by aspiration. The precipitate was resuspended in 350 µl lysis buffer RLT (with 2-mercaptoethanol). At this step, the cell lysate in the lysis buffer could be stored at −70° C. When the cell lysate was stored frozen, the lysate could be thawed by incubation at 37° C. for 10 to 15 min and, if insoluble matter was observed, centrifuged for 3 min at maximum speed to collect only the supernatant. The lysate was homogenized by syringe with a 20G Cathelin needle, and then 350-µl lysate was applied onto QIAshredder by Pipetman and centrifuged at 1500 rpm for 2 min to collect eluate. Three hundred fifty µl of 70% ethanol was added thereto and mixed well with pipetting. An RNeasy spin column was attached to the attached 2-ml tube, and the lysate mixture was applied onto the column. The column was centrifuged at 8000×g (11500 rpm) for 1 min, and the flow through was discarded. Then 700 µl of wash buffer RW1 was applied onto the column, and the column was let to stand for 5 min capped. The column was centrifuged at 11500 rpm for 15 seconds, and the flow through was discarded. The column was set onto a new 2 ml tube, and 500 µl of wash buffer RPE (containing ethanol) was applied onto the column. The column was then centrifuged at 11500 rpm for 15 sec, and the flow through was discard. Again 500 µl of wash buffer RPE was applied onto the column and centrifuged at full speed for 2 min. The column was transferred to a new tube (1.5 ml), 30 µl of DEPC treated water was applied, and the column was let to stand for 10 min capped. The column was centrifuged at 11500 rpm for 10 min to obtain total RNA. The concentration of the RNA was measured. If the amount was low, the column was set onto a new 1.5-ml tube again, 30 µl of DEPC-treated water was applied, and the column was let to stand for 10 min capped and centrifuged at 11500 rpm for 10 min.

EXAMPLE 5

DNase Treatment of the Total RNA

In order to remove DNA from the total RNA prepared from the T cells, DNase treatment was performed. The treatment was conducted in a reaction mixture containing 2 units of DNase (Nippon Gene) and 50 units of RNase inhibitor (Pharmacia) in 100 µl of 1X DNase buffer (Nippon Gene). After incubating this at 37° C. for 15 min, an equal volume of PCI (phenol:chroloform:isoamyl alcohol=25:24:1) was added thereto, and the tube was vortexed. The tube was centrifuged at 12000 rpm at room temperature for 10 min, and the upper phase (water phase) was transferred to a new 1.5 ml tube. One tenth volume of 3 M sodium acetate (pH 5.2) and 2.5 volume of 100% ethanol with 1 µl of Ethachinmate were added thereto, and the mixture was inverted several times. After allowing the tube to stand at −20° C. for 15 min, it was centrifuged at 12000 rpm for 15 min at 4° C. The supernatant was removed, and 70% ethanol was added. After tapping the tube until the precipitate was detached from the tube, the supernatant was completely removed. The precipitate was dried for 3 min and dissolved in 10 to 20 µl of DDW (DNase and RNase free). The concentration was measured, and the sample was stored at −80° C. until use.

EXAMPLE 6

Differential Display (DD) Analysis using Total RNA Prepared from T Cells

Fluorescent Differential Display (DD) analysis using total RNA prepared from T cells was carried out according to a reference (T. Ito et al., 1994, FEBS Letter. 351: 231–236). The total RNA prepared from the T cells was reverse transcribed to synthesize cDNA. For the first DD-PCR, 0.2 µg total RNA served as the template for three types of anchor primers to synthesize cDNA in separate reactions. For the second DD-PCR, 0.4 µg total RNA served as the template for three types of anchor primers to synthesize cDNA in separate reactions. In both case, the cDNAs were diluted to a final concentration equivalent to 0.4 ng/µl RNA and used for further experiments. DD-PCR was carried out using the cDNA equivalent to 1 ng of the RNA per reaction. The reaction mixture composition was as shown in Table 1.

TABLE 1

| | |
|---|---|
| cDNA (equivalent to 0.4 ng/µl RNA) | 2.5 µl |
| arbitrary primer (2 µM) | 2.5 µl |
| 10x AmpliTaq PCR buffer | 1.0 µl |
| 2.5 mM dNTP | 0.8 µl |
| 50 µM anchor primer (GT15A, GT15C, or GT15G) | 0.1 µl |
| Gene Taq (5U/µl) | 0.05 µl |
| AmpliTaq (5U/µl) | 0.05 µl |
| dH$_2$O | 3.0 µl |
| Total volume | 10.0 µl |

The PCR was Carried out as follows: 1 cycle of 95° C. for 3 min, 40° C. for 5 min, and 72° C. for 5 min; subsequently 30 cycles of 94° C. for 15 sec, 40° C. for 2 min, and 72° C. for 1 min; after these cycles, 72° C. for 5 min; and then continuously at 4° C.

For primer pairs, the anchor primer GT15A (SEQ NO ID: 2) GT15C(SEQ NO ID: 3), or GT15G (SEQ NO ID: 4), was used in combination with the arbitrary primers AG 1 to AG 110, AG 111 to AG 199, or AG 200 to AG 287, respectively, and a total of 287 combinations was tried. As for the arbitrary primers, oligomers having 10 nucleotide-long and a GC content of 50% were designed and synthesized.

For gel electrophoresis, a 6% denaturing polyacrylamide gel was prepared, and 2.5 µl of the sample from the PCR reaction was applied and run by 40 W for 210 min. After the electrophoresis, the gel was scanned by an Hitachi fluorescence imaging analyzer FMBIO II, and the gel image was obtained by detecting fluorescence.

EXAMPLE 7

Amplification of a Band Obtained from DD Analysis and Its Sequence Determination A large number of arbitrary primers were used to carry out 10% DD analysis twice. Bands that differed between the patient and normal groups or blood samples before and after pollen dispersal were selected. Reproducible bands from two experiments were excised from the gels.

One of the excised bands (called 513) was further analyzed. Band 513 was found by a DD analysis using the anchor primer GT15C(SEQ ID NO: 3) and the arbitrary primer AG136 (TCATGCAGAC/SEQ ID NO: 5).

To determine the nucleotide sequence of 513, the gel containing band 513 was excised, and the DNA was eluted in a TE solution by heating at 60° C. for 10 min. Using DNA dissolved in this TE solution as a template, PCR was conducted with the same condition as the original DD-PCR, and approximately 360 bp DNA fragment was amplified. In this PCR reaction, GT15C and AG136 were used as an anchor primer and arbitrary primer, respectively. The amplified DNA fragment was cloned into plasmid vector pCR2.1 (Invitrogen) to obtain the about 360 bp fragment harboring plasmid p513-122. The nucleotide sequence of the DNA fragment was determined using the plasmid with standard procedures.

EXAMPLE 8

Quantification using ABI-7700

The expression level of 513 was quantified by TaqMan method using ABI-PRISM7700. This method enables quantification of PCR-amplified DNA strands in real-time using fluorescence dyes.

In order to carry out the quantification, blood samples from 22 new volunteers were collected before and after cedar pollen dispersal in the spring of 1998, and total RNAs were extracted from T cells. Forty-four total RNA samples in total were used to quantify the expression of the target gene.

Using the same method as in Example 1, total IgE titer and specific IgE titers against cedar pollen, cypress pollen, and the house-dust mites *Dermatophagoides pteronyssinus* and *Dermatophagoides farinae* were measured as shown in Table 2.

TABLE 2

Specific IgE value

| | | Specific IgE (UA/ml) | | | |
|---|---|---|---|---|---|
| Subject | Time of blood collection | Cedar | Cypress | Dermatophagoides pteronyssinus | Dermatophagoides farinae | Total IgE (UA/ml) |
| A | Before dispersal | 42.7 | 5.46 | 1.09 | <0.34 | 300 |
|   | After dispersal | 83.2 | 7.85 | 1.28 | <0.34 | 460 |
| B | Before dispersal | 31.9 | 4.33 | 72.5 | 52.6 | 770 |
|   | After dispersal | 36.8 | 3.56 | 78.8 | 47.9 | 840 |
| C | Before dispersal | 15.2 | 1.5 | 68.7 | 66.1 | 450 |
|   | After dispersal | 20.3 | 1.32 | 64.3 | 49.7 | 330 |
| D | Before dispersal | 13.9 | 1.11 | 39.3 | 63.4 | 200 |
|   | After dispersal | 18.4 | 0.81 | 31.9 | 54.7 | 120 |
| E | Before dispersal | 5.25 | 0.48 | <0.34 | <0.34 | 30 |
|   | After dispersal | 8.33 | 0.46 | <0.34 | <0.34 | 38 |
| F | Before dispersal | 6.64 | 0.39 | <0.34 | <0.34 | 26 |
|   | After dispersal | 8.21 | 0.47 | <0.34 | <0.34 | 27 |
| G | Before dispersal | 1.29 | <0.34 | <0.34 | <0.34 | 26 |
|   | After dispersal | 4.02 | <0.34 | <0.34 | <0.34 | 30 |
| H | Before dispersal | 1.99 | 0.41 | 26.5 | 36.1 | 220 |
|   | After dispersal | 3.65 | 0.53 | 23.2 | 29.5 | 150 |
| I | Before dispersal | 0.93 | <0.34 | 54.6 | 51.7 | 130 |
|   | After dispersal | 3.51 | <0.34 | 43.3 | 39.9 | 100 |
| J | Before dispersal | 3.55 | 0.68 | 0.55 | <0.34 | 96 |
|   | After dispersal | 2.77 | 0.42 | 0.39 | <0.34 | 78 |
| K | Before dispersal | 1.2 | <0.34 | <0.34 | <0.34 | 96 |
|   | After dispersal | 2.72 | <0.34 | <0.34 | <0.34 | 110 |
| L | Before dispersal | 0.95 | 0.39 | 1.3 | 1.8 | 13 |
|   | After dispersal | 2.5 | 0.51 | 1.45 | 2.38 | 18 |
| M | Before dispersal | <0.34 | <0.34 | <0.34 | <0.34 | 36 |
|   | After dispersal | 2.08 | <0.34 | <0.34 | <0.34 | 43 |
| N | Before dispersal | 0.42 | <0.34 | <0.34 | <0.34 | 22 |
|   | After dispersal | 1.67 | <0.34 | 0.45 | <0.34 | 73 |
| O | Before dispersal | 0.54 | <0.34 | 28.1 | 27.2 | 180 |
|   | After dispersal | 1.42 | <0.34 | 27.2 | 26.3 | 160 |
| P | Before dispersal | 0.38 | <0.34 | 5.08 | 3.65 | 280 |
|   | After dispersal | 0.68 | <0.34 | 4.49 | 3.02 | 240 |
| Q | Before dispersal | <0.34 | <0.34 | <0.34 | <0.34 | <5.0 |
|   | After dispersal | <0.34 | <0.34 | <0.34 | <0.34 | <5.0 |
| R | Before dispersal | <0.34 | <0.34 | <0.34 | <0.34 | 53 |
|   | After dispersal | <0.34 | <0.34 | <0.34 | <0.34 | 62 |
| S | Before dispersal | <0.34 | <0.34 | <0.34 | <0.34 | 420 |
|   | After dispersal | <0.34 | <0.34 | <0.34 | <0.34 | 370 |
| T | Before dispersal | <0.34 | <0.34 | <0.34 | <0.34 | 82 |
|   | After dispersal | <0.34 | <0.34 | <0.34 | <0.34 | 62 |
| U | Before dispersal | <0.34 | <0.34 | <0.34 | <0.34 | 18 |
|   | After dispersal | <0.34 | <0.34 | <0.34 | <0.34 | 16 |
| V | Before dispersal | <0.34 | <0.34 | 0.79 | 0.81 | 180 |
|   | After dispersal | <0.34 | <0.34 | 0.78 | 0.9 | 160 |

A DD band sequence determined in Example 7 was used to design and synthesize primers 513-TQ1 (GCAGACAGTTCGATGCTTTTCC/SEQ ID NO: 6), 513-TQ2 (TTTTCTTATGAGGTCCTGCCTTG/SEQ ID NO: 7), and TaqMan probe 513-TQM (AGGGCAGTTTGCATCCTAAAGGTTGTTAAGG/SEQ ID NO: 8) for use in the quantification reaction. TaqMan probe 513-TQM was labeled with fluorescence, FAM (6-carboxyfluorescein) and TAMRA (6-carboxy-tetramethyl-rhodamine) at 5'-end and 3'-end, respectively. cDNAs were used as templates which were prepared by reverse transcription from total RNAs of 44 samples using poly-T (12 to 18 mer) as primers. To make a standard curve for the calculation of copy numbers, serial dilutions of plasmid p513-122 obtained in Example 7 was utilized as templates. The reaction mix composition for monitoring PCR amplification is shown in Table 3. To correct the difference in the cDNA concentrations between the samples, the same quantitative analysis was carried out for the β-actin gene, and its copy number was used to correct the copy number of the target gene 513.

TABLE 3

Reaction mix composition for ABI-PRISM 7700 (per well)

| Sterile distilled water | 25.66 (μL) |
|---|---|
| 10x TaqMan buffer A | 5 |
| 25 mM MgCl$_2$ | 7 |
| dATP (10 mM) | 1.2 |
| dCTP (10 mM) | 1.2 |
| dGTP (10 mM) | 1.2 |
| dUTP (10 mM) | 1.2 |
| Forward Primer (100 μM) | 0.15 |
| Reverse Primer (100 μM) | 0.15 |
| 513 TaqMan probe (6.7 μM) | 1.49 |
| AmpliTaq Gold (5U/μL) | 0.25 |
| AmpErase UNG (1U/μL) | 0.5 |
| Template solution | 5 |
| Total volume | 50 |

The copy number of gene 513 in each of the samples corrected with β-actin copy number is shown in Table 4. The correction was performed by calculating average copy number of β-actin from all the samples and by dividing the copy number of gene 513 in each sample by the relative value of the copy number of β-actin in each sample when the average copy number was set at 1.

TABLE 4

Quantification of data by ABI7700 (copy/ng RNA)
Data corrected with beta-actin

| Subject | Time of blood collection | Band ID 513 |
|---|---|---|
| A | Before dispersal | 661 |
|   | After dispersal | 871 |
| B | Before dispersal | 2880 |
|   | After dispersal | 640 |
| C | Before dispersal | 530 |
|   | After dispersal | 403 |
| D | Before dispersal | 1273 |
|   | After dispersal | 433 |
| E | Before dispersal | 636 |
|   | After dispersal | 692 |
| F | Before dispersal | 665 |
|   | After dispersal | 1391 |
| G | Before dispersal | 692 |
|   | After dispersal | 350 |
| H | Before dispersal | 1137 |
|   | After dispersal | 361 |
| I | Before dispersal | 1169 |
|   | After dispersal | 1717 |
| J | Before dispersal | 1846 |
|   | After dispersal | 891 |
| K | Before dispersal | 443 |
|   | After dispersal | 1007 |
| L | Before dispersal | 1742 |
|   | After dispersal | 539 |
| M | Before dispersal | 721 |
|   | After dispersal | 440 |
| N | Before dispersal | 459 |
|   | After dispersal | 342 |
| O | Before dispersal | 662 |
|   | After dispersal | 455 |
| P | Before dispersal | 409 |
|   | After dispersal | 472 |
| Q | Before dispersal | 542 |
|   | After dispersal | 662 |
| R | Before dispersal | 422 |
|   | After dispersal | 25 |

TABLE 4-continued

Quantification of data by ABI7700 (copy/ng RNA)
Data corrected with beta-actin

| Subject | Time of blood collection | Band ID 513 |
|---|---|---|
| S | Before dispersal | 435 |
|   | After dispersal | 332 |
| T | Before dispersal | 610 |
|   | After dispersal | 449 |
| U | Before dispersal | 687 |
|   | After dispersal | 455 |
| V | Before dispersal | 679 |
|   | After dispersal | 368 |

A two-way layout analysis of variance was conducted using these data. The test was carried out according to the two factors: (1) before and after pollen dispersal and (2) the group that showed 3.5 AU/ml or more at least once in two measurements of each specific IgE in the sera (the high IgE group) and the other group (the normal IgE group). The number of subjects in each group was, for example, in the case of cedar pollen, 10 people in the high IgE group and 12 people in the normal IgE group. Another test was carried out for total IgE using the group that showed 200 AU/ml and the other group. A two-way layout analysis of variance was performed using StatView software (Abacuus Concepts, Inc.).

Figure 2:
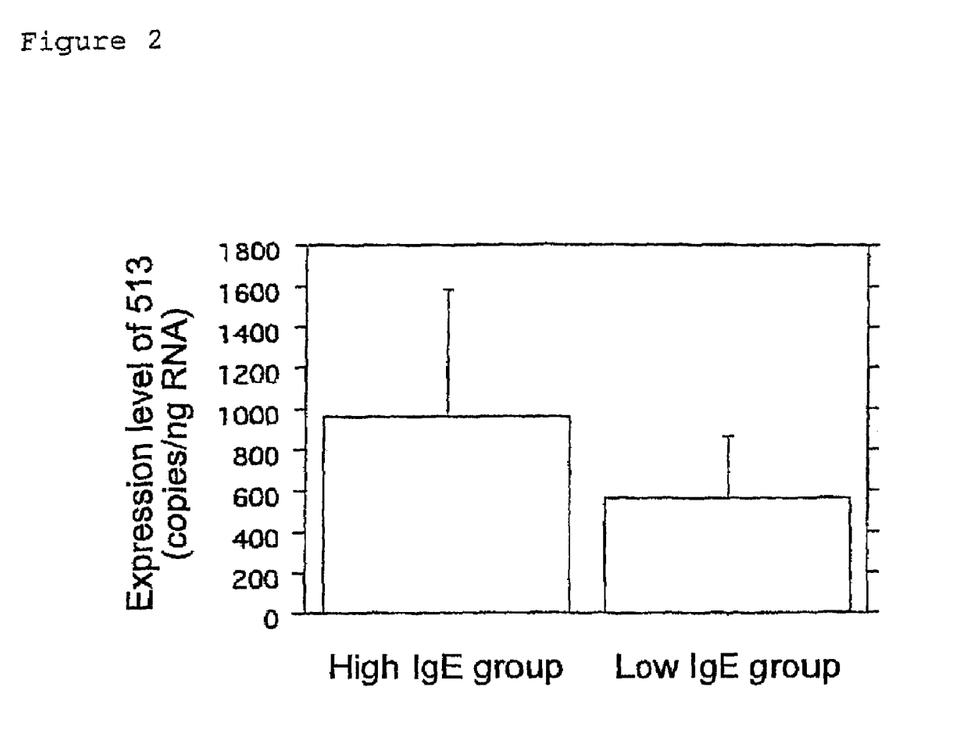
FIG. 2 shows the expression changes of gene 513 between a high IgE group and a normal IgE group that are grouped according to cedar pollen specific IgE titers. Error bars indicate standard deviation.

As a result, when the IgE titer was grouped against cedar pollen, a significantly higher level of gene 513 expression was seen in the high IgE group compared to the normal IgE group (Table 5 and FIG. 2). When this result was combined with the IgE data obtained before and after pollen dispersal, the expression level of gene 513 in the high IgE group and the normal IgE group were 961.8±626.1 and 556.7±311.8 copies/ng RNA (average±standard deviation), respectively.

TABLE 5

513

| | | | Two-way layout analysis of variance P value | | |
|---|---|---|---|---|---|
| | Classification | | IgE high/low | Before dispersal/ after dispersal | Interaction of two factors |
| Specific IgE | Cedar | | 0.0100 | 0.0663 | 0.5189 |
| | Cypress | | 0.0408 | 0.0518 | 0.0907 |
| | Dermatophagoides pteronyssinus | | 0.2043 | 0.0606 | 0.2496 |
| | Dermatophagoides farinae | | 0.2043 | 0.0606 | 0.2496 |
| Total IgE | | | 0.7893 | 0.0582 | 0.1872 |
| t-test | | | | 0.0622 | |

EXAMPLE 9

Cloning of Gene 513 and Nucleotide Sequence Analysis

Gene 513 was cloned using a Marathon cDNA Amplification Kit (CLONTECH). mRNAs of YY-1 cell line were used to synthesize cDNA to be used as templates for the Marathon kit. According to the 513 nucleotide sequence isolated by DD analysis, specific primer 513_154L (GCT-TGTCCCTGGGGTTCACACTT/SEQ ID NO: 9) was designed to use with the adapter primer attached to the kit. The PCR was carried out, and up to approximately 1.1-kb amplification products were amplified. The nucleotide sequence of the fragment was found to be 1171 bp and contained the previously determined sequence. This sequence is shown as SEQ ID NO: 1.

INDUSTRIAL APPLICABILITY

The present invention provided a novel gene that correlates with cedar pollen specific IgE titer. Using the expression of the gene of the present invention as an index, it is possible to test for whether a subject has an allergic diathesis or not, and to screen for a candidate compound for a therapeutic drug for a allergic disease.

What is claimed is:

1. A method of testing for a cedar pollen allergy in a human subject, said method comprising the steps of:
   (a) preparing T cells from the subject,
   (b) preparing an RNA sample from said T cells,
   (c) conducting hybridization with said RNA sample using a probe consisting of the complement of a segment of SEQ ID NO:1, optionally wherein the probe is linked to a label or vector nucleic acid, and
   (d) measuring the amount of RNA that is derived from said subject and that hybridizes with said probe, and comparing said amount of RNA with the amount of RNA of a control group which has 3.5 AU/mL or less of cedar pollen specific IgE, wherein if the amount of gene 513 RNA is significantly higher in a sample from the subject than in the control group, then the subject is determined to have a cedar pollen allergy.

2. A method of testing for a cedar pollen allergy in a human subject, said method comprising the steps of:
   (a) preparing T cells from the subject,
   (b) preparing an RNA sample from said T cells,
   (c) synthesizing cDNA by conducting reverse transcription reaction with said RNA sample,
   (d) conducting polymerase chain reaction (PCR) using said cDNA as template and a primer consisting of a segment of gene 513 SEQ ID NO:1 or the complement thereof, optionally wherein the primer is linked to a label, and
   (e) comparing the amount of DNA amplified by said PCR with a control group which has 3.5 AU/mL or less of cedar pollen specific IgE, wherein if the amount of gene 513 cDNA is significantly higher in a sample from the subject than in the control group, then the subject is determined to have a cedar pollen allergy.

3. The method of claim 2, wherein said PCR is carried out by a PCR amplification monitoring method.

4. The method of claim 1, wherein said T cells are prepared from peripheral blood of said subject.

5. The method of claim 1, wherein the probe consists of at least 15 nucleotides of SEQ ID NO:1 or the complement thereof.

6. The method of claim 2, wherein the primer consists of at least 15 nucleotides of SEQ ID NO:1 or the complement thereof.

* * * * *